United States Patent [19]

Lombard

[11] 4,366,437
[45] Dec. 28, 1982

[54] DEVICE FOR MEASURING THE AMOUNT OF OXYGEN IN COMBUSTION GASES

[75] Inventor: Claude Lombard, Le Chesnay, France

[73] Assignee: Regie Nationale des Usines Renault, Boulogne-Billancourt, France

[21] Appl. No.: 193,296

[22] Filed: Oct. 2, 1980

[30] Foreign Application Priority Data

Oct. 10, 1979 [FR] France ................ 79 25175

[51] Int. Cl.$^3$ ............................................. G01N 27/00
[52] U.S. Cl. ........................................ 324/464; 324/463
[58] Field of Search ............... 324/459, 463, 464, 465

[56] References Cited

U.S. PATENT DOCUMENTS

| | | | |
|---|---|---|---|
| 2,864,998 | 12/1958 | Lee | 324/463 |
| 3,411,073 | 11/1968 | Marr | 324/463 |
| 3,713,773 | 1/1973 | Fontijn | 324/464 |

*Primary Examiner*—Michael J. Tokar
*Attorney, Agent, or Firm*—Oblon, Fisher, Spivak, McClelland & Maier

[57] ABSTRACT

A device for measuring the amount of oxygen in combustion gas including succesively, a channel bordered by two plates between which exists a magnetic field, a central electrode divided in two, longitudinally, a gas discharge path, and finally a mechanism for measuring the current or ionization potential in each of the paths. This device is, accordingly, applicable to the automobile industry and automation and regulation of the operation of boilers of all kinds.

5 Claims, 1 Drawing Figure

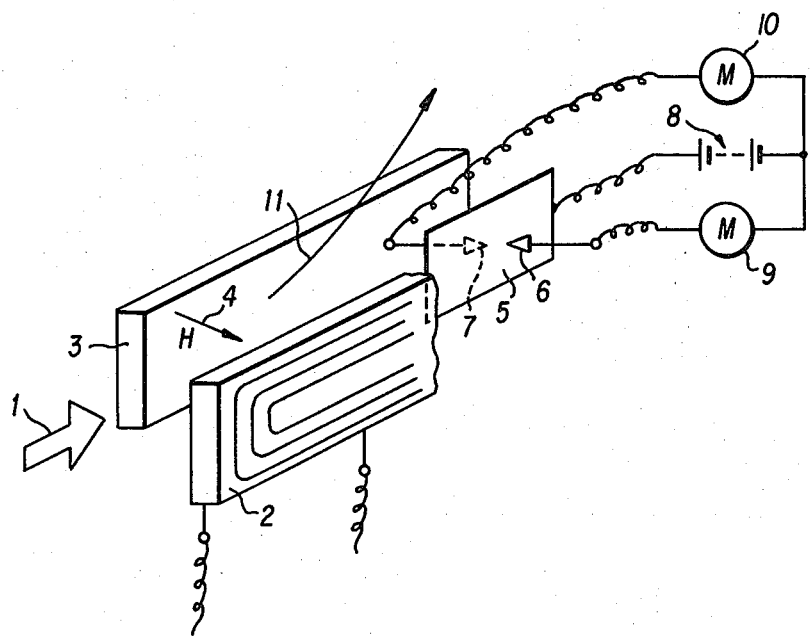

DEVICE FOR MEASURING THE AMOUNT OF OXYGEN IN COMBUSTION GASES

BACKGROUND OF THE INVENTION

1. Field of the Invention

The present invention relates to a device for measuring the oxygen content in combustion gases. More particularly it relates to a device for measuring the oxygen content of combustion exhaust gases of an internal combustion motor wherein the device is capable, therefore, of being substituted advantageously for a probe. The device according to the invention may also be located at the outlet of a boiler of some type in order to regulate and/or automate its function.

2. Description of the Prior Art

It has been suggested to use the ionization potential difference between oxygen and the other gases in the air, notably nitrogen, to measure the oxygen content, especially in combustion gases.

In selecting an intermediate value for the applied potential, one may gather a current between the electrodes depending on the oxygen content. Unfortunately this current depends more on the temperature and humidity than on the oxygen content, such conduit requiring different structures in which normal air is sent between (among) a system of electrodes with the air being analyzed in another system. Putting such systems into effect is delicate if one wants to balance the temperature and the humidity level, without which balancing differential devices have little advantage.

SUMMARY OF THE INVENTION

The present invention has as its object the provision for a device for measuring the oxygen content without the prior art inconveniences, i.e. being concerned about the effect of temperature and humidity. It includes a mechanism for measuring the currents or ionization potentials of gases and a mechanism allowing a magnetic field to be produced which deflects the path of oxygen molecules. This has in effect a slight magnetic susceptibility already used for twenty or more years in analyzers based on principles other than those of the present invention, e.g. measuring pressure differentials. Combining ionization and magnetic field makes it possible to obtain the stated objective in two ways which differ no more than in the number and the placement of the electrodes.

The first consists in periodically applying the deviatory magnetic field which passes between the electrodes for ionic measuring of first normal gases and then gases enriched with oxygen.

The second consists in allowing the constant magnetic field to separate the circulation channel into two gas zones, one enriched with oxygen and the other deficient or normal, each zone having its proper measure of current or ionization potential which is then comparable to the other. This method makes it possible to use permanent magnets to produce the field although the first can use magnets if they are movable, specifically rotatable. The attached drawing shows a possible embodiment not intended to restrict the scope of the invention. It corresponds to the second method in which the magnetic field is permanent. It is only given as an embodiment.

BRIEF DESCRIPTION OF THE DRAWING

Various objects, features and attendant advantages of the present invention will become self-evident from a review of the FIGURE wherein:

The Sole FIGURE shows one embodiment of the present invention.

DETAILED DESCRIPTION OF THE PREFERRED EMBODIMENTS

As shown in the Sole FIGURE, a gas stream arrives as denoted by reference number 1 and passes between two plates 2 and 3 which creates a magnetic field H, according to arrow 4, between one another. The plates 2 and 3 are magnets with a strong force field, flat coils of electromagnets, or any other equivalent device. At the extremity opposite arrow 1 there is positioned a central electrode 5 which separates the gas path into two parts.

Starting from and separate from the central electrode 5 and at a reasonable distance from it are two electrodes 6 and 7 the form of which allows the easy emission of ions when the central plate is charged to a potential greater than that of the ionization of oxygen. The electrodes 6 and 7 are, by way of examples, one or more terminal points, a line stretched parallel to plate 5, etc.

Electrodes 5, 6, 7 are connected to a power source 8 and to two elements for measuring current or potential, 9 and 10. The oxygen molecules attracted by the magnetic field are diverted toward one of the plates 2 or 3 which thus increases the oxygen concentration in the portion of the gas stream adjacent one of the plates 2 or 3. This results in a separation or stratification of gases in the stream which changes the ionization conditions between one of the electrodes 6 or 7 and the central electrode 5. The dissemetry between the charges received respectively by the electrodes 6 and 7 is raised until it is greater than the content of oxygen in the burning gases arriving at the entrance 1. The ionized particles which may continue to arrive into the gas as indicated by reference number 1 are deflected along arrow 11 or its direction and do not, therefore, disturb the measurement.

In the case where the electrodes 2 and 3 are electromagnets, it is up to the technician to regulate their supply of electrical current so as to modify or periodically interrupt the magnetic field by means of a time base and/or an appropriate commutation circuit.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A device for measuring the oxygen content in a flow of combustion gases, comprising:
   deflection means in the path of said flow of combustion gases for producing a magnetic field in said flow, whereby oxygen in said flow is at least partially deflected by said magnetic field towards an oxygen rich concentration portion of said flow; and
   means for measuring ionization potential of gases in said flow path at a point downstream from said deflection means in the direction of said flow, said means for measuring including means for separately measuring the ionization potential of gases in said oxygen concentration portion of said flow.

2. A measuring device according to claim 1, said deflection means comprising first and second electrodes and further comprising means for modifying the magnetic field present between said first and second electrodes.

3. The device of claims 2 or 1 including at least one element for physically separating said oxygen rich concentration portion from the remainder of said flow.

4. The device of claims 2 or 1 wherein said means for measuring further includes means for separately measuring the ionization potential of gases not in said oxygen rich concentration portion of said flow.

5. The device of claim 2 wherein said means for modifying includes means for periodically interrupting said magnetic field.

* * * * *